United States Patent
Winer (10) Patent No.: US 9,629,680 B2
(45) Date of Patent: Apr. 25, 2017

(54) STERILE DRAPE FOR ROBOTIC SURGICAL EQUIPMENT

(71) Applicant: Ecolab USA Inc., St. Paul, MN (US)

(72) Inventor: Marilyn Winer, Denville, NJ (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 14/533,196

(22) Filed: Nov. 5, 2014

(65) Prior Publication Data

US 2015/0047647 A1 Feb. 19, 2015

Related U.S. Application Data

(62) Division of application No. 13/712,208, filed on Dec. 12, 2012, now Pat. No. 8,910,637.

(51) Int. Cl.
*A61B 19/00* (2006.01)
*A61B 19/08* (2006.01)
*A61B 46/00* (2016.01)
*A61B 46/10* (2016.01)

(52) U.S. Cl.
CPC ............ *A61B 19/081* (2013.01); *A61B 46/00* (2016.02); *A61B 46/10* (2016.02)

(58) Field of Classification Search
CPC ..... A61B 19/08; A61B 19/081; A61B 19/088; A61B 19/10; A61B 19/20; A61B 19/22; A61B 19/2203; A61B 2019/084; A61B 2019/085; A61B 46/00; A61B 46/10; A61B 46/20; A61B 46/205; A61B 46/23; A41D 13/12
See application file for complete search history.

(56) References Cited

U.S. PATENT DOCUMENTS

| | | | | |
|---|---|---|---|---|
| 3,528,720 A | * | 9/1970 | Treace | 359/510 |
| 3,540,441 A | * | 11/1970 | Collins | 128/855 |
| 3,707,964 A | * | 1/1973 | Patience et al. | 128/856 |
| 3,747,655 A | * | 7/1973 | Hadtke | 108/90 |
| 3,777,749 A | * | 12/1973 | Collins | 128/855 |
| 3,952,738 A | * | 4/1976 | Krzewinski | 128/855 |
| 3,955,569 A | * | 5/1976 | Krzewinski et al. | 128/855 |
| 4,457,026 A | * | 7/1984 | Morris | 2/171 |

(Continued)

FOREIGN PATENT DOCUMENTS

WO WO8501496 4/1985

*Primary Examiner* — Kari Petrik
*Assistant Examiner* — Raymond E Harris
(74) *Attorney, Agent, or Firm* — Merchant & Gould P.C.

(57) ABSTRACT

A sterile surgical drape for protecting a robotic surgical system includes an oblong drape of a clear flexible plastic material, which unfolds from a compact packet. From the proximal side of the main panel of the drape there project two pocket flaps, which are separated by a medial trough. The two pocket flaps are configured to slip over one another and together enclose the top of the control tower in an overlapping fashion, such that the robotic manipulator arms extend on either side of the main panel, while the camera/endoscope arm extends through the medial trough. The open ends of the pocket flaps are folded over to form cuffs, wherein a nurse can insert his/her hand to draw the flap over the top of the tower without touching non-sterile surfaces. The unfolding of the main panel is controlled by adhesive tabs or tear strips, so that the bottom of the panel does not engage the cart's wheels or the floor.

11 Claims, 6 Drawing Sheets

(56) References Cited

U.S. PATENT DOCUMENTS

| | | | |
|---|---|---|---|
| 5,515,868 A | 5/1996 | Mills | |
| 5,522,403 A | 6/1996 | Bark et al. | |
| 5,860,420 A * | 1/1999 | Wiedner et al. | 128/853 |
| 6,105,578 A * | 8/2000 | Sommers et al. | 128/849 |
| 6,116,741 A * | 9/2000 | Paschal | 359/510 |
| 6,123,080 A | 9/2000 | Mohan et al. | |
| 6,923,186 B2 * | 8/2005 | Gavette et al. | 128/854 |
| 7,727,244 B2 * | 6/2010 | Orban et al. | 606/130 |
| 7,886,743 B2 | 2/2011 | Cooper et al. | |
| 7,992,560 B2 | 8/2011 | Burton et al. | |
| 8,206,406 B2 * | 6/2012 | Orban, III | 606/130 |
| 8,216,250 B2 * | 7/2012 | Orban et al. | 606/130 |
| 8,813,755 B2 * | 8/2014 | Hoffmann | 128/849 |
| 2003/0106493 A1 | 6/2003 | Christian et al. | |
| 2011/0041995 A1 * | 2/2011 | Adams | 156/250 |
| 2011/0259347 A1 * | 10/2011 | Zurn | 128/849 |

\* cited by examiner

STERILE DRAPE FOR ROBOTIC SURGICAL EQUIPMENT

CROSS REFERENCE TO RELATED APPLICATIONS

The present application is a divisional application of U.S. patent application Ser. No. 13/712,208, filed Dec. 12, 2012 and issued as U.S. Pat. No. 8,910,637, which application is incorporated herein by reference.

BACKGROUND OF THE INVENTION

The present invention relates to the field of sterile surgical drapes, and more particularly to sterile surgical drapes designed to protect portions of a robotic surgical system.

The use of robotic systems has become increasingly common in various surgical procedures, including prostate, cardiac, gynecological, and gastrointestinal surgeries. Among the major advantages of robotic surgery are precision, miniaturization, smaller incisions, decreased blood loss, less pain, and quicker healing time. Robotic systems enable enhanced articulation and three-dimensional magnification, resulting in improved ergonomics. Other benefits of robotic techniques include reduced duration of hospital stays, fewer transfusions and decreased use of pain medication.

In the case of robotically-assisted minimally-invasive surgery, instead of directly manipulating the instruments, the surgeon controls the instruments either through a direct tele-manipulator or through computer control. A tele-manipulator is a remote manipulator that allows the surgeon to perform the normal movements associated with the surgery while one or more robotic arms carry out those movements using manipulators to perform the actual surgery on the patient. In computer-controlled systems, the surgeon uses a remote computer to control the robotic arms and its manipulators.

One widely-used robotic surgical system is the da Vinci™ Surgical System, marketed by Intuitive Surgical Inc. This system comprises a surgeon's control console, a patient-side robotic cart, and a high-definition 3D vision system. The robotic cart is equipped with four arms manipulated by the surgeon—one camera arm to control the camera/endoscope and three manipulator arms to control surgical instruments. Articulating surgical instruments are mounted on the robotic manipulator arms and are introduced into the body through cannulas. The da Vinci™ system senses the surgeon's hand movements and translates them electronically into scaled-down micro-movements to manipulate the tiny surgical instruments. The system also detects and filters out any tremors in the surgeon's hand movements, so that they are not replicated robotically. The system's camera/endoscope transmits a true stereoscopic picture to the surgeon's console. The da Vinci™ System is FDA approved for a variety of surgical procedures, including surgery for prostatectomies, hysterectomies and mitral valve repairs, and it is used in numerous hospitals throughout the world.

During the preparation of a robotic surgical apparatus for an operative procedure, it is necessary to cover or drape the robotic arms to protect them from contamination by blood or other bodily fluids. Failure to do this properly results in a need to decontaminate and sterilize the robotic arms after the surgery, which is difficult due to the complex articulation of the apparatus. While sleeve-type fitted drapes are available for the robotic arms themselves, there currently exists no drape to cover the central tower from which the robotic arms extend. Consequently, it is often necessary to decontaminate this tower after the robotic surgery.

The principal problem associated with devising a cover for the tower of a robotic surgical system is interference with the mobility of the robot arms connected to the tower. In the da Vinci™ system, for example, the three manipulator arms extend from the sides of the central tower, while the camera/endoscope arm extends from the front of the tower. Therefore, a sleeve-type drape over the tower would interfere with all four arms, while even a simple sheet drape would impede the central camera arm. The prior art in the field of surgical draping affords no means of addressing this problem.

A number of patent documents teach various sleeve-type covers for protecting the surgical robotic arms themselves. Examples of these are the U.S. patent of Mohan et al. (U.S. Pat. No. 6,123,080), the U.S. patent application of Christian et al. (2003/0106493), and the international patent application of AT&T (WO85/01496). But a sleeve-type drape as applied to the central tower of a da Vinci™-type robotic would restrict the movement of the manipulator arms as well as the central camera arm.

While the U.S. patent of Cooper et al. (U.S. Pat. No. 7,886,743) describes a sterile drape that encloses the control mechanism of a surgical robotic arm, the robotic arm must extend around the periphery of the drape, so that there is no provision for the movement of a central arm through the drape. The sterile surgical drape described in the U.S. patent application of Orban III et al. (U.S. Pat. No. 7,727,244) includes dual enclosures which cover both a single peripheral robotic arm and the control mechanism. However, this design cannot accommodate multiple robotic arms and would constrain a central camera arm extending from the control mechanism.

The principal objective of the present invention is to provide a sterile surgical drape that covers and protects the central tower of a surgical robotic cart, such as the robotic cart of the da Vinci™ Surgical System, while leaving unconstrained all of the robotic arms extending from the central tower.

SUMMARY OF THE INVENTION

The present invention comprises an oblong drape of a clear flexible plastic material which unfolds from a compact packet. From the proximal side of the main panel of the drape there project two pocket flaps, which are separated by a medial trough. The two pocket flaps are configured to slip over one another and together enclose the top of the control tower in an overlapping fashion, such that the robotic manipulator arms extend on either side of the main panel, while the camera/endoscope arm extends through the medial trough. The open ends of the pocket flaps are folded over to form cuffs, wherein a nurse can insert his/her hand to draw the flap over the top of the tower without touching non-sterile surfaces. The unfolding of the main panel is controlled by adhesive tabs or tear strips, so that the bottom of the panel does not engage the cart's wheels or the floor.

The foregoing summarizes the general design features of the present invention. In the following sections, a specific embodiment of the present invention will be described in some detail. This specific embodiment is intended to demonstrate the feasibility of implementing the present invention in accordance with the general design features discussed above. Therefore, the detailed description of this embodiment is offered for illustrative and exemplary purposes only,

DETAILED DESCRIPTION OF THE PREFERRED EMBODIMENT

Figure 1:
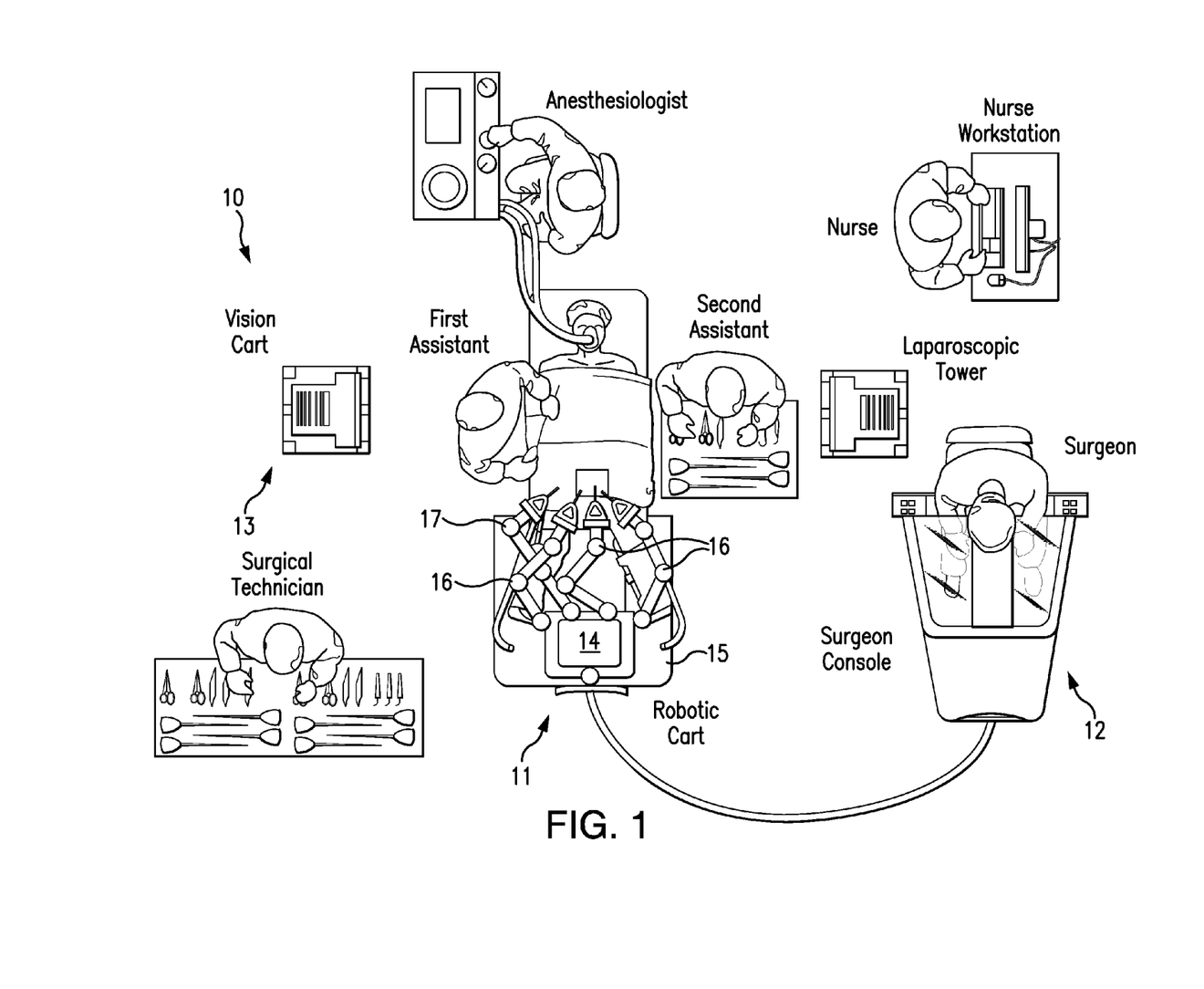
FIG. 1 is a plan view of an exemplary operating room utilizing a robotic surgical system.
Figure 2:
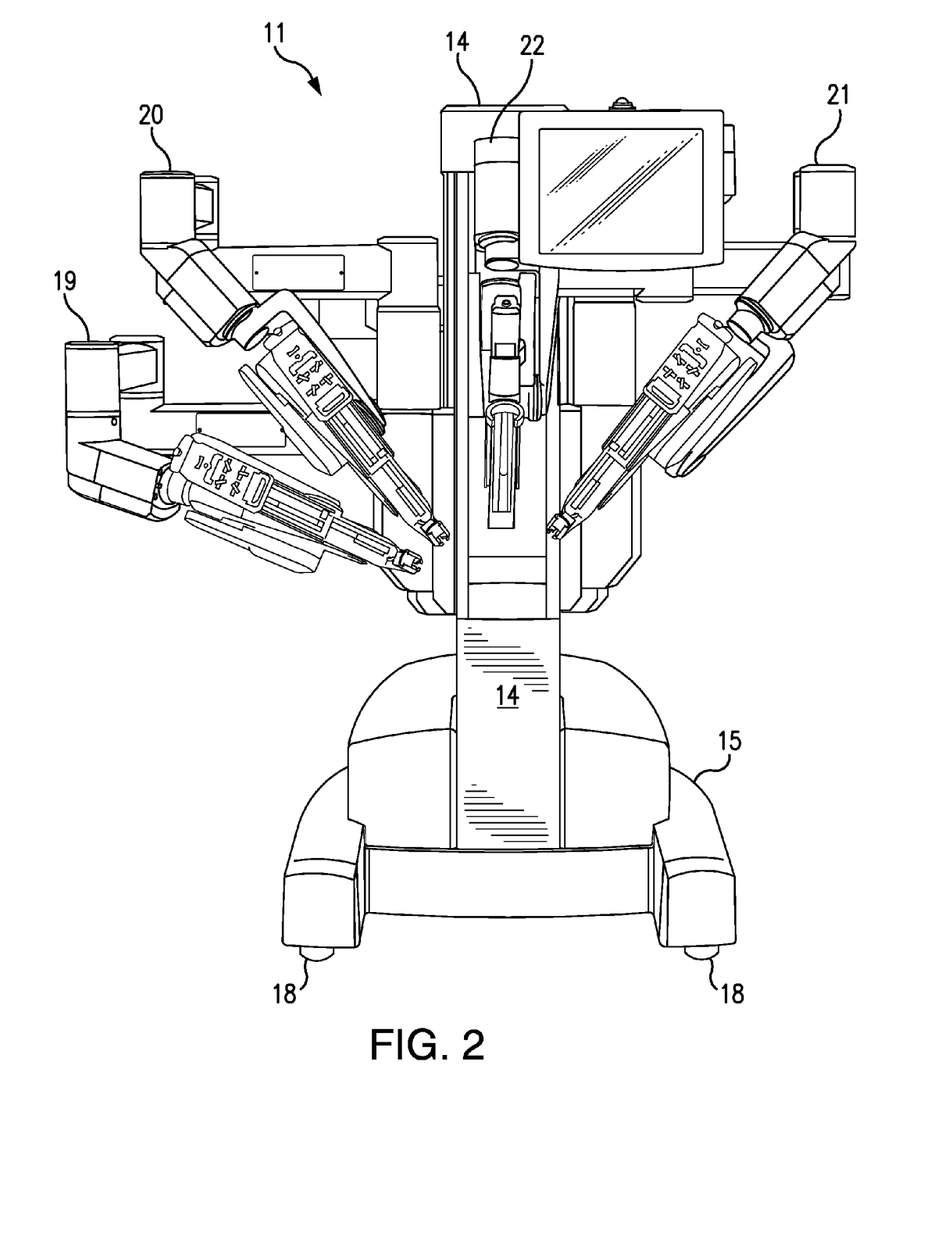
FIG. 2 is a front perspective view of a robotic cart of the da Vinci™ Surgical System.

Referring to FIG. 1, an exemplary robotic surgical system 10, based upon the da Vinci™ Surgical System, comprises a robotic cart 11, a surgeon console 12, and a vision cart 13. The robotic cart 11 comprises a central tower 14, a base 15, three robotic manipulator arms 16, and a central camera/endoscope arm 17. Referring to FIG. 2, the exemplary robotic cart 11 has a vertical central tower 14 supported on a mobile base 15, which moves about on wheels 18. From the right side of the tower 14 extend a first manipulator arm 19 and a second manipulator arm 20, while a third manipulator arm 21 extends from the left side of the tower 14. From the front face of the tower 14 extends the camera/endoscope arm 22.

Figure 3:
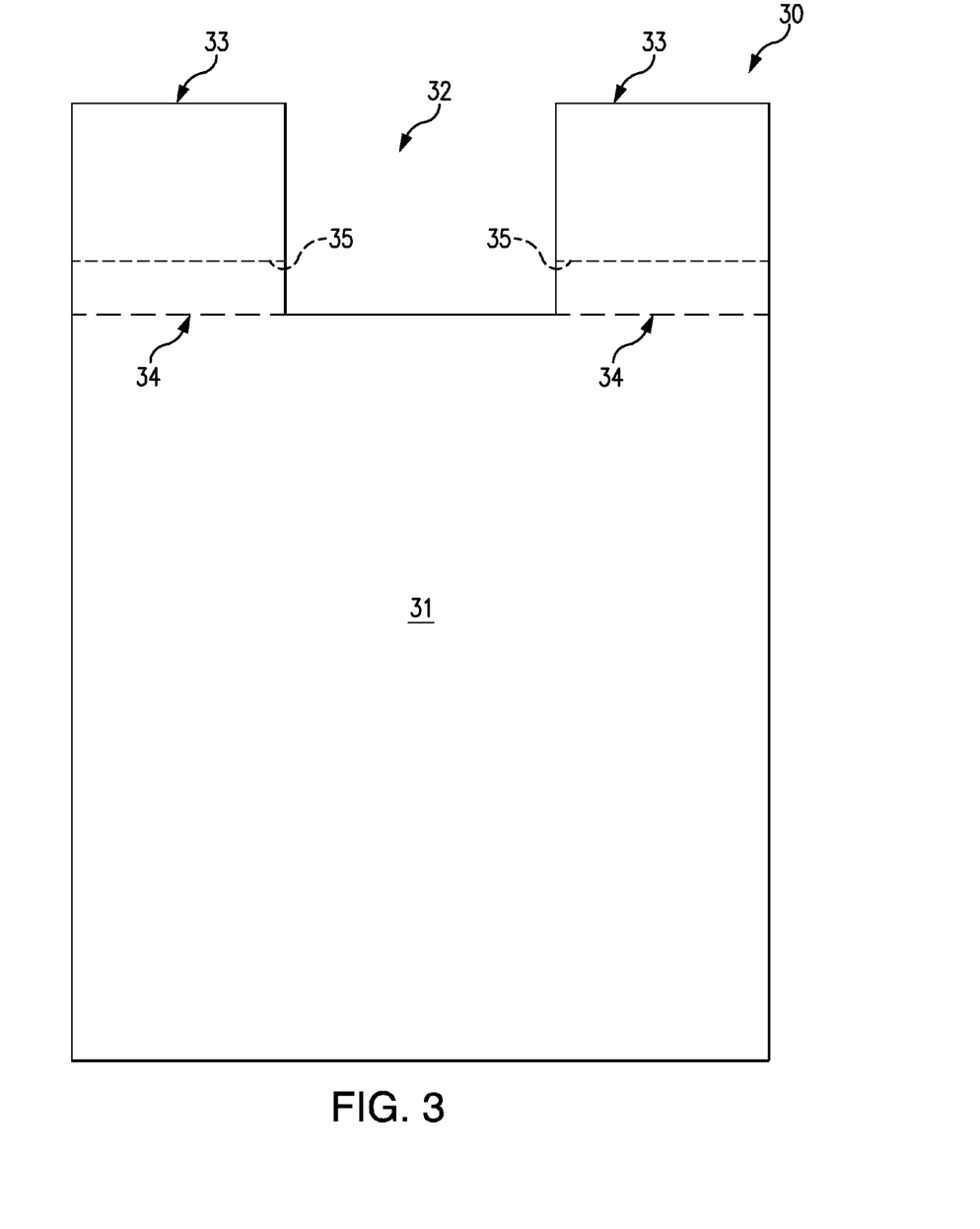
FIG. 3 is a plan view of an exemplary sterile surgical drape according to the preferred embodiment of the present invention.

Referring to FIG. 3, a sterile surgical drape 30 is a flexible sheet of transparent plastic, preferably made of clear low-density polyethylene of 2 to 6 mils thickness. The drape 30 is oblong, preferably rectangular, with an oblong main panel 31, preferably rectangular, and a cut-out 32, preferably rectangular, on its proximal side. On either side of the cut-out 32, the drape 30 has two pocket flaps 33, preferably squares, which are formed by doubling over the plastic on the flaps 33. Each of the pocket flaps 33 has a flap opening 34, above which is formed a cuff 35.

As applied to the da Vinci™ Surgical System, the optimal dimensions of the drape 30 are as follows: main panel 31, 6 to 8 feet long by 5 ½ to 7 ½ feet wide; cut-out 32, 18 to 30 inches long by 24 to 36 inches wide; pocket flaps 33, 18 to 30 inches length and width.

Figure 4A:
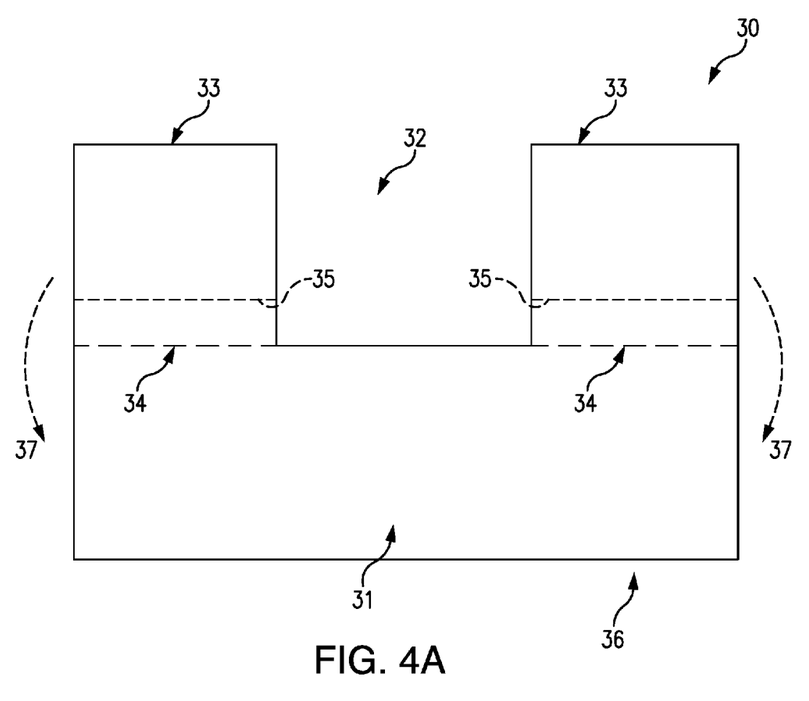
FIG. 4A is a plan view of the sterile surgical drape of FIG. 3 in the first stage of being folded into an exemplary compact packet.
Figure 4B:
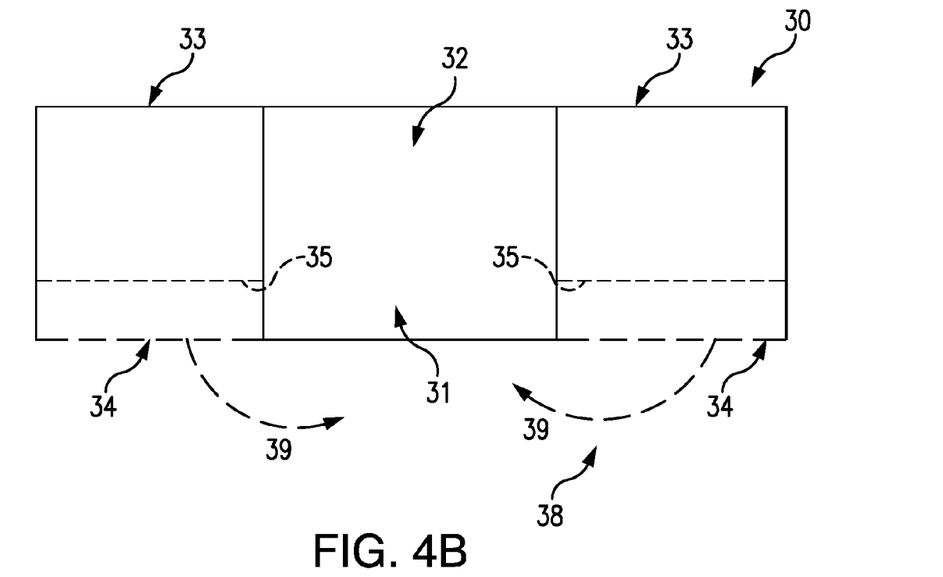
FIG. 4B is a plan view of the sterile surgical drape of FIG. 3 in the second stage of being folded into an exemplary compact packet.
Figure 4C:
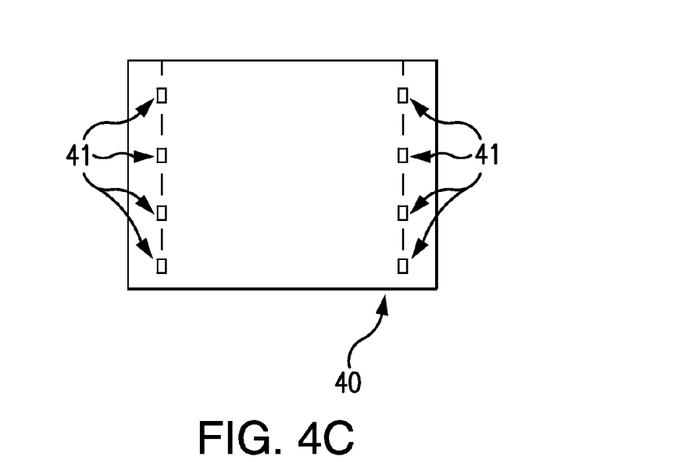
FIG. 4C is a plan view of the sterile surgical drape of FIG. 3 after being folded into an exemplary compact packet.

FIGS. 4A, 4B and 4C illustrate one way in which the drape 30 is can be folded into a compact packet 40. As shown in FIG. 4A, the main panel 31 is first folded upward several times until it is approximately the same length as the pocket flaps 33, thereby arriving at a horseshoe-shaped configuration 36. Then, the two pocket flaps 33 are folded down 37 over the folded main panel 31, thereby arriving at a tri-fold configuration 38, which is shown in FIG. 4B. Finally, the two pocket flaps 33 are folded inward 39 over the cut-out 32, thereby arriving at the compact packet configuration 40. The various folds within the compact packet 40 are secured by adhesive tabs 41, which are removed as the packet 40 is unfolded.

Figure 5:
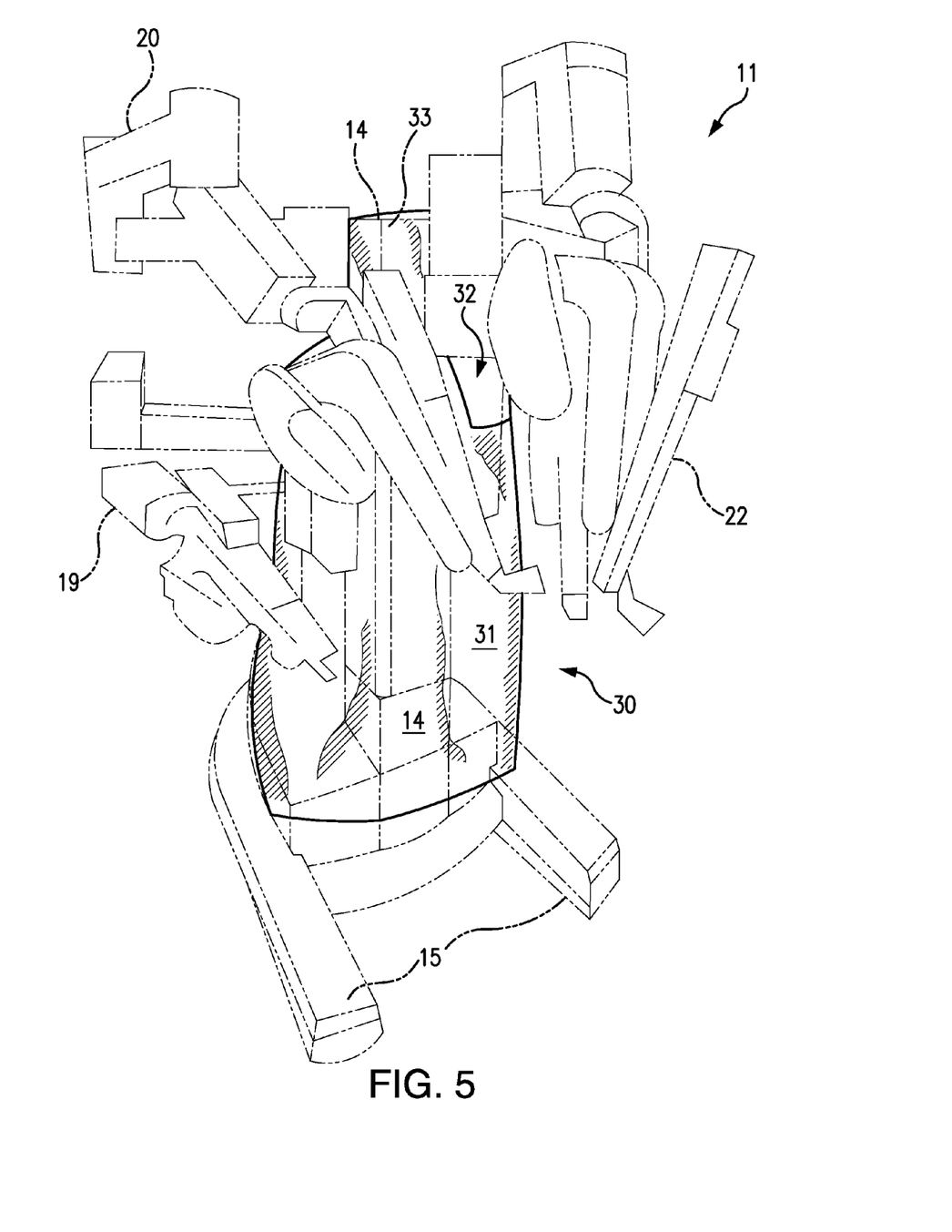
FIG. 5 is a perspective view of an exemplary sterile surgical drape according to the preferred embodiment of the present invention covering the central tower of a robotic cart of the da Vinci™ Surgical System, which is shown in ghost view.

FIG. 5 illustrates how the drape 30 is used to cover the central tower 14 of a robotic cart 11 of the da Vinci™ Surgical System. The compact packet 40 is first opened into the horseshoe configuration 36, and the cut-out 32 is aligned under the central camera/endoscope arm 22. The two pocket flaps 33 of the drape 30 are then placed over the top of the tower 14 so that they overlap one another. In placing the flap openings 34 over the top of the tower 14, the operating room nurse inserts his/her hand into an opening of the cuffs 35 above the flap openings 34 in order to avoid contact with non-sterile surfaces. The main panel 31 is then unfolded by releasing the adhesive tabs 41 until the drape 30 extends downward to just above the mobile base 15 of the cart 11. The 5 drape 30 is extended so that the main panel 31 remains within the peripheral robotic manipulator arms 19-21, thereby leaving the movement of those arms unimpeded. The cart 11 can then be wheeled into position for the surgery. Once the cart 11 is in position, the main panel 31 can be unfolded further downward to cover the bottom of the tower 14.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A sterile surgical drape for protecting a surgical robot, wherein the drape comprises:

a main panel comprising a substantially rectangular plastic sheet having a width between 5.5 and 7.5 feet and a first edge and a second edge opposite of the first edge, the first and second edges defining a length;

two flaps extending from the first edge and defining together with the first edge a center opening between the two flaps, each flap forming a pocket accessible through a flap opening along the first edge and each pocket comprising a folded cuff accessible through an opening above the flap opening, wherein each of the flaps is substantially square having a width of about 18 to 30 inches and the center opening has a height of about 18 to 30 inches and a width of about 24 to 36 inches:

wherein:

the sterile surgical drape is sized and constructed to cover a central tower of the surgical robot on at least one side of the central tower, wherein one or more robotic arms extend from the central tower, and the sterile surgical drape is sized and constructed not to impede with movement of the robotic arms;

each of the pockets is constructed to be capable of receiving a hand of a surgical attendant through the flap opening; and the sterile surgical drape is constructed so that the flaps are capable of being slid, one overlapping the other, over a top of the central tower to cover the top of the central tower and to hold the sterile surgical drape in place, while the main panel and the flaps cover non-sterile surfaces of the central tower at least on one side and the central opening is sized and constructed so that at least one of the robotic arms can extend through the central opening.

2. The sterile surgical drape of claim 1 further comprising a plurality of adhesive tabs for holding the sterile surgical drape in a folded configuration during storage.

3. The sterile surgical drape of claim 2, wherein the adhesive tabs are positioned on the sterile surgical drape so that the adhesive tabs are capable of holding the sterile surgical drape in a partially folded configuration while the sterile surgical drape is assembled on the surgical robot.

4. The sterile surgical drape of claim 3, wherein the length of the main panel is shortened by folding in the partially folded configuration.

5. The sterile surgical drape of claim 1, wherein the surgical robot comprises at least one robotic arm extending from a first side of the central tower, at least one robotic arm extending from a second side of the central tower, and at least one robotic arm extending from a front of the central tower, and wherein the sterile surgical drape is sized and constructed to cover the central tower without covering the robotic arms.

6. The sterile surgical drape of claim 5, wherein the robotic arm extending from the front of the central tower comprises a camera, and wherein the robotic arm extending from the front of the central tower can extend through the central opening.

7. The sterile surgical drape of claim 1, wherein the drape is folded into a compact packet having multiple folds that are secured by multiple adhesive tabs, and wherein the drape is constructed and assembled to be unfolded from the compact packet by successively releasing or removing the adhesive tabs so that the drape covers the at least one side of the central tower.

8. The sterile surgical drape of claim 1, wherein the flaps are formed from plastic sheet.

9. The sterile surgical drape of claim 1, wherein at least one robotic arm is attached to the central tower at an attachment point having a height, and wherein the length of the main panel substantially corresponds to the height of the attachment point.

10. The sterile surgical drape of claim 1, wherein the length is between 6 and 8 feet.

11. The sterile surgical drape of claim 1, wherein the drape is in a partially folded configuration comprising a plurality of folds on the main panel secured by adhesive tabs and the two flaps extending outwardly from the first edge of the main panel forming a horse-shoe shape.

* * * * *